(12) United States Patent
Hallén et al.

(10) Patent No.: US 8,047,708 B2
(45) Date of Patent: Nov. 1, 2011

(54) DEVICE, METHOD AND VESSEL ASSEMBLY FOR THE MEASUREMENT OF HEAT FLOW AT LEAST ONE SAMPLE

(75) Inventors: Dan Hallén, Vallingby (SE); Ingemar Wadsö, Lund (SE)

(73) Assignee: Symcel Sverige AB, Kista (SE)

( * ) Notice: Subject to any disclaimer, the term of this patent is extended or adjusted under 35 U.S.C. 154(b) by 541 days.

(21) Appl. No.: 12/227,869

(22) PCT Filed: May 29, 2007

(86) PCT No.: PCT/SE2007/050368
§ 371 (c)(1),
(2), (4) Date: Dec. 1, 2008

(87) PCT Pub. No.: WO2007/139498
PCT Pub. Date: Dec. 6, 2007

(65) Prior Publication Data
US 2009/0092169 A1    Apr. 9, 2009

(30) Foreign Application Priority Data
May 30, 2006   (SE) ...................................... 0601217

(51) Int. Cl.
*G01K 17/00* (2006.01)
*G01K 1/00* (2006.01)
*G01K 13/00* (2006.01)
*G01N 25/00* (2006.01)

(52) U.S. Cl. ............ 374/29; 374/141; 374/208; 374/43; 374/33

(58) Field of Classification Search .................. 374/141, 374/208, 29, 43, 33
See application file for complete search history.

(56) References Cited

U.S. PATENT DOCUMENTS

| 4,095,453 | A | 6/1978 | Woo |
| 6,096,272 | A | 8/2000 | Clark et al. |
| 6,265,226 | B1 * | 7/2001 | Petro et al. ........................ 506/12 |
| 2002/0098592 | A1 * | 7/2002 | Neilson et al. ................... 436/147 |
| 2003/0026736 | A1 * | 2/2003 | Hajduk et al. .............. 422/82.12 |
| 2003/0118078 | A1 * | 6/2003 | Carlson et al. ................. 374/160 |
| 2005/0036536 | A1 * | 2/2005 | Lewis .............................. 374/2 |
| 2011/0064613 | A1 * | 3/2011 | Chen ............................ 422/62 |

FOREIGN PATENT DOCUMENTS
| EP | 0 033 961 | 8/1981 |
| WO | WO 94/01217 | 1/1994 |
| WO | WO 03/008942 | 1/2003 |

OTHER PUBLICATIONS

International Search Report for PCT/SE2007/050368, mailed Jul. 10, 2007.

* cited by examiner

*Primary Examiner* — Lisa Caputo
*Assistant Examiner* — Mirellys Jagan
(74) *Attorney, Agent, or Firm* — Nixon & Vanderhye P.C.

(57) ABSTRACT

The present invention relates to a device and a method for the measurement of heat flow from at least one sample. The device 1 is adapted to receive a multi well vessel assembly (2) with samples in one or several vessels (21, 22, . . . 2n). The device (1) comprises an opening (11) for insertion of the vessel assembly (2) into the device (1), a measurement chamber (12) with a heat sink (13), a channel (14) extending from the opening (11) to the measurement chamber (12). The present invention specifically teaches that the opening (11) and channel (14) leads horizontally into the device (1), and that the height of the opening (11), channel (14) and measurement chamber (12) is only high enough to receive the vessel assembly (2).

33 Claims, 2 Drawing Sheets

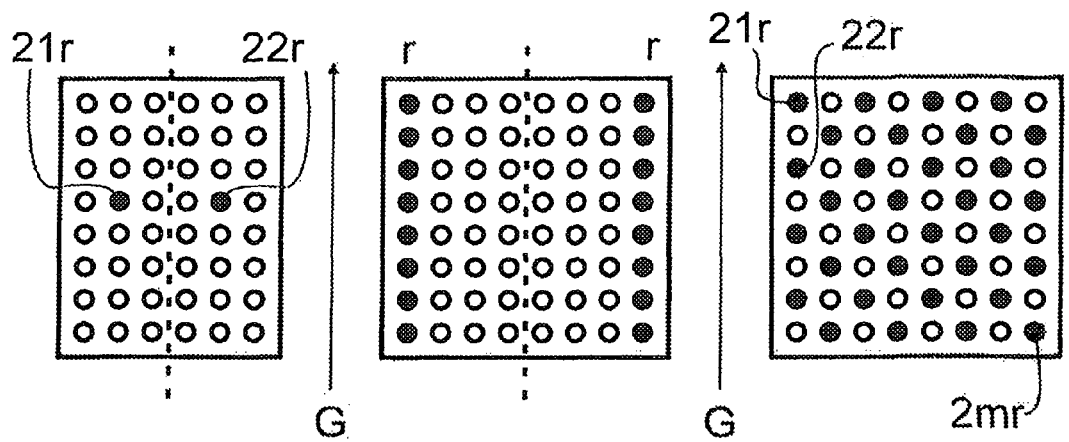
*Fig. 4a.*     *Fig. 4b.*     *Fig. 4c.*
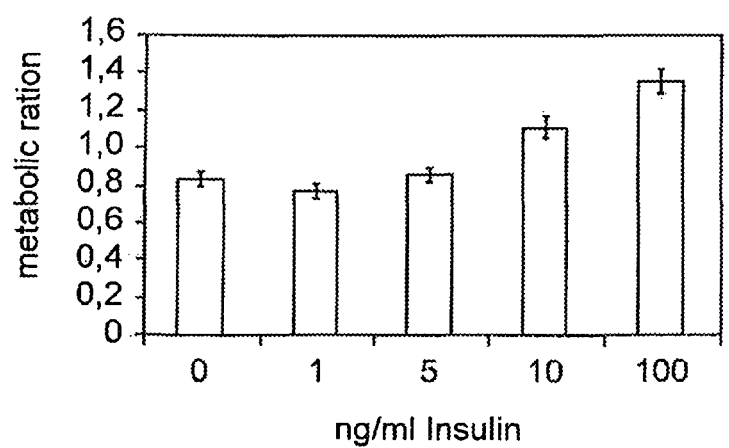
*Fig. 5.*

US 8,047,708 B2

DEVICE, METHOD AND VESSEL ASSEMBLY FOR THE MEASUREMENT OF HEAT FLOW AT LEAST ONE SAMPLE

This application is the U.S. national phase of International Application No. PCT/SE2007/050368, filed 29 May 2007, which designated the U.S. and claims priority to Sweden Application No. 0601217-3, filed 30 May 2006, the entire contents of each of which are hereby incorporated by reference.

FIELD OF INVENTION

The present invention relates to a device and a method for the measurement of heat flow from at least one sample. The device is adapted to receive a multi well vessel assembly with samples in one or several vessels. The device comprises an opening for insertion of the vessel assembly into the device, a measurement chamber with a heat sink, a channel extending from the opening to the measurement chamber and a lid for closing the opening during measurements. The present invention also relates to a vessel assembly adapted to be used in an inventive device or method.

DESCRIPTION OF THE BACKGROUND ART

In most physical, chemical and biological processes result in a change in the heat content of the system. Calorimetry is the methodology to directly measure changes in heat content. Calorimetric instruments are used in widespread application in physics, chemistry and biology. From calorimetric data fundamental thermodynamic properties such as internal enthalpy change, $\Delta H$, heat capacity change, $\Delta Cp$, and absolute heat capacity, $Cp$, can be obtained. Further analysis of data can indirectly give other thermodynamic properties such as Gibbs free energy change, $\Delta G°$, and entropy change, $\Delta S°$. For more complex systems calorimetric instruments are used for monitoring thermal events as an indicator of complex or unknown processes occurring in the samples.

There are mainly two commercial calorimetric methodologies—isothermal calorimetry and scanning calorimetry. Scanning calorimetry means that the temperature of the calorimetric device is actively changed, while for isothermal calorimetry the temperature is nearly constant or changed by the heat adsorbed or produced by the process in the calorimeter.

Due to sample specific needs or methodological reasons the commercial calorimetric available instruments are more or less specialized for specific areas of interest in physics, chemistry and biology. There are for example differential scanning calorimeters (DSC) that are specialized for solid samples and others for liquid solutions or mixtures. There are calorimeters designed for use at low, high temperature applications as well as in the temperature rang 0-120° C. There are instruments designed for solely titration at isothermal conditions (ITC).

Presently, industrial calorimetric applications are mainly related to material science issues regarding manufacturing control and physical or chemical stability of products. Biological processes are often connected with changes in metabolic activity, which are manifested by changes in heat as a result from oxidative processes on cellular level. The type of biological material that have been studied by isothermal calorimetry are for example mammalian cells, plant cells, prokaryotic cells, mammalian tissues, plant tissues and whole organisms. Examples on cellular events that have been studied by calorimetry are mitosis, necrosis, apoptosis, and induced changes in metabolic activity. The applications have potential to be applied biological industrial areas among others such as eukaryotic and prokaryotic protein production, drug discovery, drug development and clinical work (see e.g. Beezer, A. E., et al (1993) Microbios. 73, 205-213, Beezer, A. E. (1990) Tokai J Exp Clin Med. 15, 369-372, Monti, M. (1990 Thermochimica Acta 172, 53-60, and Takahashi, K. (1990) Tokai J Exp Clin Med. 15, 387-394). One important reason for this is that the methodology presents data as real-time data, which is a common demand on new technologies for biological applications.

All methods and technologies for the life science industrial organizations need to have high sample through put with simple sample handling. In order to satisfy industrial needs the methods have to be based upon parallel multiple sample detection, preferably as array system. The commercial calorimetric instruments that are available have that in common that the samples are individually loaded or inserted into the calorimeter. There are a few commercial available multi-channel calorimeters which all have individual calorimetric channels that share a common thermostat.

There is a number of multi-channel calorimeters described that either use resistance thermometry, i.e. temperature determination by thermistor resistor thermometer or platinum resistor thermometer, or thermal detection of electrothermal voltage determination, as described in patent publications US2004/0107986, US2005/0241869, US2005/0036536 and US2004/0038228. There are microcalorimeters described that are based on thermopile chips, se US2004/0038228 and Maskow, T. et al. (2006) J. Biotechnol. 122, 431-42. These types of instruments are characterized by high sensitivity, small sample volumes (a few micro liters), fast response, and appearing to be suitable for multi-channel designs. However, in many applications the sample volumes are too small, e.g. in experiments with a monolayer of cells, for non-homogenous samples like soil and with samples like tissues, organs and animals. Further, for heat conduction calorimeters the detection limit for a certain type of sample is proportional to the amount of material contained in the vessel. For materials with very low specific thermal powers it may therefore be necessary to conduct the measurements with sample volumes much larger than a few micro liters. There are security demands and cost effectiveness demands from industrial users that the samples are contained in and experiments performed in disposable sample containers. The chip technology has not yet been able to handle this problem.

Thermopile heat-conduction calorimeters can be used for measuring high sensitivity changes in heat content from samples in which physical, chemical or biological processes occur. The heat is measured by measuring the heat flow from a sample, through a thermopile, to a thermostated heat sink. This principle of measuring heat has not yet been shown to be compatible with multiple removable, and therefore disposable, multiple sample vessels in array format. The reasons for this have been difficulties in (i) ensuring good thermal equilibration of the inserted body of an array when inserting an array into the measuring chamber, (ii) avoiding dramatic thermal and mechanical, i.e. pressure, disturbances of thermostating blocks and heat-sink when inserting an array into the measuring chamber, and (iii) ensuring high thermal conductivity connection between a removable array of multiple vessels and heat-flow sensors, such as thermopiles. Regardless if it is a single vessel container or an array of multiple vessel containers, the sample container needs to be introduced into the calorimetric measuring chamber in more than one step in order to obtain thermal equilibrium and stable calorimetric signal within sufficient time. The calorimetric sample vessels are vertically inserted into calorimetric devices. For an array of multiple vessel containers this way of insertion causes poor and long equilibration time thermal equilibration. It also causes large disturbances of the thermopiles, due to piezoelectric response of the thermopiles.

Accordingly, there is a need for a calorimetric instrument that is based upon an array system where the sample containers are disposable. The instrument should be simple to handle and with high sensitivity according to the demands of the users.

SUMMARY OF THE PRESENT INVENTION

Problems

From the standpoint of the technical background it is a technical problem to achieve high measurement stability in a measurement chamber using a multichannel device for heat flow measurements. The multiple channels require a large opening into the device and the space above the samples in the measurement chamber is large and thus hard to keep stable with regards to temperature.

It is possible to insert a body on top of the samples in the measurement chamber, the body being stabilised to the temperature in the measurement chamber, thus further stabilising the measurement chamber and decreasing the space above the samples. However, the insertion of such a body will cause pressure variations and varying air flows in the measurement chamber that will cause unwanted temperature variations and that will require long time periods for equilibration before measurement. It is thus a problem to provide a measurement chamber that is large enough to receive a multi well vessel assembly with a maintained control of the measurement environment, or at least with a minimised disturbance of the measurement environment when inserting the vessel assembly.

It is a problem to provide a device that presents an effective insertion of samples into the measurement chamber with regards to how fast the samples can be inserted and how soon measurements can start after insertion of the samples into the measurement chamber.

Heat flow measurements requires a stable and controlled environment, and under these conditions it is a problem to provide a possibility to both increase and decrease the temperature in the measurement chamber in a controlled manner and according to required testing temperatures with maintained temperature stability in the measurement camber.

It is a problem to provide a measurement chamber where several wells or vessels can be used in parallel and where each vessel is monitored individually.

It is also a problem to provide a multi well vessel assembly adapted to the parallel measurement of several individual samples in a device for heat flow measurements.

Solution

With the purpose of solving one or more of the above identified technical problems, the present invention teaches that with a device for the measurement of heat flow from at least one sample, where the device is adapted to receive a multi well vessel assembly with samples in one or several vessels, where the device comprises an opening for insertion of the vessel assembly into the device, a measurement chamber with a heat sink, a channel extending from the opening to the measurement chamber and a lid, with a closing member, for closing the opening during measurements, it is proposed that the opening and channel leads horizontally into said device in order to facilitate the possibility to minimise the height of the opening, the channel and the measurement chamber so that it is only high enough to receive the vessel assembly. Thereby it is possible to have a very small measurement chamber without a large space above the vessels.

It is proposed that the height of the opening, channel and measurement chamber exceeds the height of the vessel assembly by 5 mm or less.

In order to provide a device that presents an effective insertion of samples into the measurement chamber, with regards to how fast the samples can be inserted and how soon measurements can start after insertion of the samples into the measurement chamber, the present invention teaches that the measurement chamber is made out of a cavity within a first metal body, that the channel is made out of a hole through a second metal body, and that the first and second metal bodies are thermally isolated from each other. It is also proposed that the heat sink is made out of a third metal body positioned within the cavity and thermally isolated from the first metal body. In order to further improve the control of the environment in the measurement chamber it is proposed that the measurement chamber is divided into a first area, adapted for equilibration of a vessel assembly, and a second area, containing the heat sink and adapted to receive a vessel assembly during the measurement.

In order to provide a possibility to monitor several individual vessels in a vessel assembly the present invention teaches that thermal sensors are positioned on the heat sink so that every individual vessel within a vessel assembly is positioned on a thermal sensor as a vessel assembly is placed in the second area. For the purpose of isolating the different thermal sensors from each other it is proposed that the top surface of the third metal body is divided into pillars, and that one of the thermal sensors is positioned on top of each pillar.

It is proposed that the first and second metal body and the lid are thermostated at the same temperature for the purpose of further improving the environment in the measurement chamber.

These metal bodies can be kept at constant temperature at a chosen experimental temperature for isothermic measurements or the temperature of the metal bodies can be changed over a chosen temperature range for scanning measurements.

With the purpose of allowing heat to leave the heat sink and the measurement chamber it is proposed that an outer container encloses the first and second metal bodies, and that the container is thermally isolated from the first and second metal bodies. This outer container may be a Dewar container. The outer container, with its first and second metal bodies, is positioned within an outer chamber, and the temperature within the outer chamber is kept at a lower temperature than that of the measurement chamber. This temperature is in the order of 5° C. or more below the temperature in the measurement chamber. This will cause a heat flow from the heat sink and out to the outer chamber, with the outer container as a buffer to prevent too much cooling of the measurement chamber, which heat flow will make it easier to control the environment within the measurement chamber.

With the purpose of enable the device to receive vessel assemblies of different heights it is proposed that the height of the channel and measurement chamber is adaptable to the height of different vessel assemblies.

The present invention also relates to a vessel assembly with several vessels for the containing of samples, the vessel assembly being adapted to an inventive device. It is proposed that the outer bottom surface of each vessel is formed to provide a good thermal contact with a thermal sensor when put into an inventive device.

It is specifically proposed that each vessel within the vessel assembly is positioned so that they will be positioned on a thermal sensor when put into an inventive device.

Since there might be difficulties in positioning all thermal sensors in the device at an exactly even level, and since it is of outmost importance that each vessel is in contact with its respective thermal sensor, it is proposed that each vessel is loosely fit into the vessel assembly, thus enabling each vessel to get in direct contact with its respective thermal sensor.

The vessels might be made out of different materials depending on different parameters, such as what kind of samples that is to be contained in the vessels or what cost that is acceptable for a vessel. It is proposed that the vessels are made out of glass, stainless steel or plastic.

It is also proposed that the vessel assembly is disposal or that the vessels of the vessel assembly are disposal.

The present invention also relates to a method to measure the heat flow from at least one sample in a multi well vessel assembly, by means of a device comprising an opening for inserting said vessel assembly into the device, a measurement chamber with a heat sink, a channel extending from the opening to the measurement chamber and a lid for closing the opening during measurements. The invention teaches that the vessel assembly is transported in a horizontal direction through the opening and channel, and into the measurement chamber, which will make it possible to use an opening and measurement chamber that is only high enough to receive the vessel assembly.

The inventive method proposes that, with the purpose of achieving an acceptable stability in the measurement chamber, the vessel assembly is allowed to equilibrate in the channel before being transported into the measurement chamber, that it is allowed to equilibrate in a first area within the measurement chamber before being transported into a second area, containing the heat sink and adapted to receive a vessel assembly for measurements, and that the vessel assembly is allowed to equilibrate in the second area before the start of said measurement. It is proposed that the vessel assembly is allowed to equilibrate for a time period in the order of 10 minutes in the channel and said first area, and for a time period in the order of 30 minutes in the second area.

The inventive method teaches that the channel and measurement chamber are kept constant at a chosen experimental temperature for isothermic measurements and that the temperature of the channel and measurement chamber is changed over a chosen temperature range for scanning measurements.

In order to obtain a relevant reference temperature for a measurement it is proposed that at least one of the vessels is used as a reference vessel, and that the reference vessel is charged with inert material. It is possible to chose any number of reference vessels out of the existing vessels in the vessel assembly, and it is proposed that half of the vessels are used as reference vessels and half of the vessels are used for samples.

With the purpose of enabling cooling of the temperature in the measurement chamber it is proposed that the temperature within an outer chamber, within which the outer container is positioned, is kept at a lower temperature than that of the measurement chamber. The temperature difference between the outer chamber and the measurement chamber might for instance be in the order of 5° C. or more.

Advantages

The advantages of a device and a vessel assembly, or a method, according to the present invention are that the present invention provides a controlled and stable measurement environment for heat flow measurements in several parallel vessels. The present invention also provides a fast measurement procedure where the measurements may start in the order of 50 minutes from when the vessel assembly was inserted into the device.

BRIEF DESCRIPTION OF THE DRAWINGS

A device, a vessel assembly and a method according to the present invention will now be described in more detail with reference to the accompanying drawings, in which:

FIGS. 4a, 4b and 4c are a schematic and simplified top views of vessel assemblies with different setups of reference vessels, and FIG. 5 is a diagram showing the results from a measurement performed according to a possible embodiment of the present invention.

DETAILED DESCRIPTION OF EMBODIMENTS AS PRESENTLY PREFERRED

Figure 1:
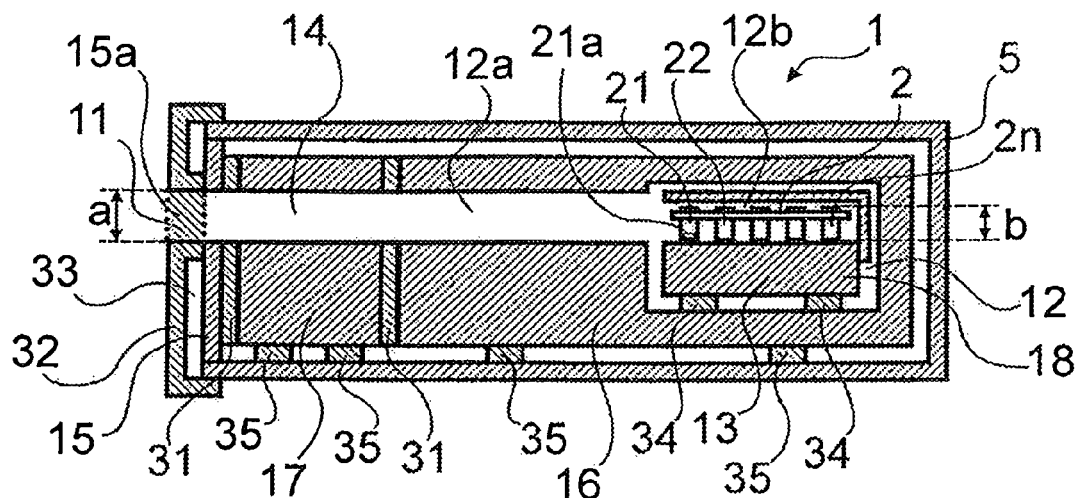
FIG. 1 is a schematic and highly simplified cross sectional side view of a device according to the present invention.

The present invention will now be described in more detail and with reference to FIG. 1, where a device 1 for the measurement of heat flow from at least one sample 21a is shown, the device 1 being adapted to receive a multi well vessel assembly 2 with samples in one or several vessels 21, 22, . . . , 2n.

The device 1 comprises an opening 11 for insertion of the vessel assembly 2 into the device 1, a measurement chamber 12 with a heat sink 13, a channel 14 extending from the opening 11 to the measurement chamber 12, a lid 15 for closing the opening during measurements, and a closing member 15a schematically shown in dotted lines in the figure.

The present invention specifically teaches that the opening 11 and channel 14 leads horizontally into the device 1, thus making it possible to have a relatively small opening 11 into the device 1. It is desirable to have the opening 11 as small as possible and the present invention teaches that the height "a" of the opening 11, the channel 14 and the measurement chamber 12 is only high enough to receive the vessel assembly. One proposed embodiment teaches that the height "a" of the opening 11, the channel 14 and the measurement chamber 12 exceeds the height "b" of the vessel 2 assembly by 5 mm or less.

In order to provide a stable measurement environment it is proposed that the measurement chamber 12 is made out of a cavity within a first metal body 16, that the channel 14 is made out of a hole through a second metal body 17, and that the first and second metal bodies 16, 17, and the lid 15 are thermally isolated from each other. This can be achieved by first plastic members 31 that are positioned between the first and second metal body 16, 17, and between the second metal body 17 and the lid 15, these first plastic members 31 having a high thermal resistance. Thermal isolation of the lid 15 from the outer environment can be achieved by a plastic lid 32 which is isolated from said lid 15 by an air gap 33.

It is also proposed that the heat sink 13 is made out of a third metal body 18 positioned within the cavity, and that this third metal body 18 is thermally isolated from the first metal body 16. This can be achieved by second plastic members 34, with high thermal resistances, that are positioned between the first and third metal body 16, 18.

The measurement chamber 12 is divided into a first area 12a, adapted for equilibration of a vessel assembly 2, and a second area 12b, containing the heat sink 13 and adapted to receive a vessel assembly 2 during the measurement.

Figure 2:
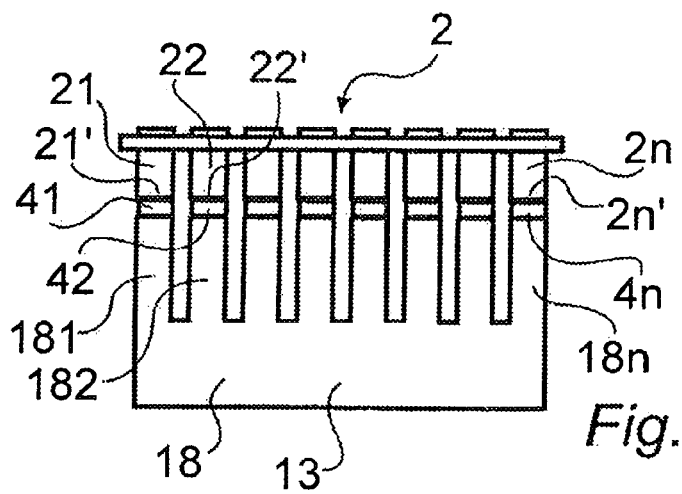
FIG. 2 is a schematic side view of a heat sink with thermal elements and a vessel assembly.

FIG. 2 is a somewhat enlarged view of a vessel assembly 2 standing on a heat sink 13. It is schematically shown that thermal sensors 41, 42, . . . , 4n are positioned on the heat sink 13 so that every individual vessel 21, 22, . . . , 2n within a vessel assembly 2 is positioned on a thermal sensor 41, 42, . . . , 4n as a vessel assembly 2 is placed in the second area 12b. It is also proposed that the top surface of the third metal body 18 could be divided into pillars 181, 182, . . . , 18n, and that one of the thermal sensors 41, 42, . . . , 14n is positioned on top of each pillar 181, 182, . . . , 18n.

In order to overcome any height differences that might be caused by the fact that the thermal sensors 41, 42, . . . , 4n are not all of the same height it is proposed that the thermal sensors might be spring loaded on top of the heat sink 13 to ensure a good thermal contact between respective sensor and vessel.

The present invention also proposes that the first and second metal body 16, 17 and the lid 15, 15a are thermostated at the same temperature.

An inventive device 1 may be used for different kinds of measurements, and depending on the purpose of the measurement it is proposed that the metal bodies 16, 17, 18 are kept at constant temperature at a chosen experimental temperature for isothermic measurements or that the temperature of the metal bodies 16, 17, 18 is changed over a chosen temperature range for scanning measurements.

With the purpose of further stabilising the environment of the measurement chamber 12 FIG. 1 shows that an outer container 5 encloses the first and second metal bodies 16, 17, which container is thermally isolated from the first and second metal bodies 16, 17 by means of third plastic members 35. One proposed embodiment teaches that the outer 5 container is a Dewar container.

Figure 3:
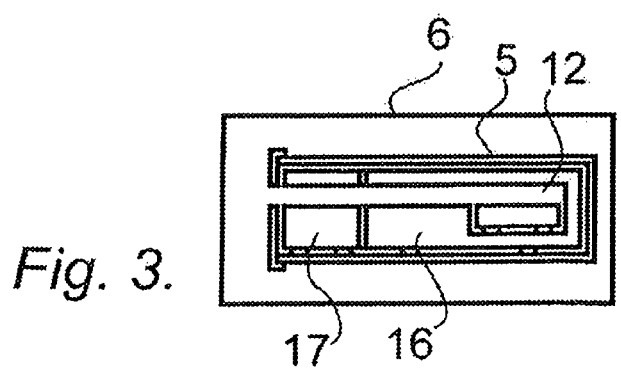
FIG. 3 is a schematic and highly simplified side view of an inventive device with an outer chamber.

FIG. 3 shows an embodiment where the outer container 5, with its first and second metal bodies 16, 17, is positioned within an outer chamber 6, where the temperature within the outer chamber 6 is kept at a lower temperature than that of the measurement chamber 12, thus enabling cooling of the measurement chamber during regulation of the temperature. The temperature in the outer chamber 6 might be in the order of 5° C. or more below the temperature in the measurement chamber 12.

One proposed embodiment of the present invention teaches that the height "a" of the channel 14 and measurement chamber 12 might be adaptable to the height "b" of different vessel assemblies 2.

With renewed reference to FIG. 2 an inventive multi well vessel assembly 2 with several vessels 21, 22, . . . , 2n for the containing of samples 21a is illustrated. The present invention specifically teaches that the outer bottom surface 21', 22', . . . , 2n' of each vessel 21, 22, . . . , 2n is formed to provide a good thermal contact with a thermal sensor 41, 42, . . . , 4n when put into an inventive device 1. Each vessel 21, 22, . . . , 2n within the vessel assembly 2 is positioned so that they will be positioned on a thermal sensor 41, 42, . . . , 4n when put into an inventive device 1.

In order to overcome any difference in height between the individual thermal sensors 41, 42, . . . , 4n in a device 1, it is proposed that each vessel 21, 22, . . . , 2n is loosely fit into the vessel assembly 2, whereby each vessel is adjustable to the height of their respective thermal sensor.

The vessels 21, 22, . . . , 2n within a vessel assembly 2 may be in different materials. It is for instance possible to have vessels made out of glass, stainless steel or plastic.

It is also proposed that the complete vessel assembly 2 is disposal or that the individual vessels 21, 22, . . . , 2n of the vessel assembly 2 are disposal.

With renewed reference to FIG. 1 an inventive method will now be described. The invention refers to a method to measure the heat flow from at least one sample 21a in a multi well vessel assembly 2 by means of a device 1 comprising an opening 11 for inserting the vessel assembly 2 into the device 1, a measurement chamber 12 with a heat sink 13, a channel 14 extending from the opening 11 to the measurement chamber 12, a lid 15 for closing the opening 11 during measurements, and a closing member 15a schematically shown in the figure. The inventive method teaches that the vessel assembly 2 is transported in a horizontal direction through the opening 11 and channel 14, and into the measurement chamber 12.

The inventive method proposes that the vessel assembly 2 is allowed to equilibrate in the channel 14 before being transported into the measurement chamber 12, and that the vessel assembly 2 is allowed to equilibrate in a first area 12a within the measurement chamber 12 before being transported into a second area 12b, the second area 12b containing the heat sink 13 and being adapted to receive a vessel assembly 2 for measurements. It is also proposed that the vessel assembly 2 is allowed to equilibrate in the second area 12b before the start of the measurement. The time period for equilibration could be in the order of 10 minutes in the channel 14 and first area 12a, and in the order of 30 minutes in the second area 12b.

It should be noted that it is possible to regulate the temperature in different ways depending on what types of measurements that are to be made. It is for instance possible to keep the temperature in the channel 14 and measurement chamber 12 constant at a chosen experimental temperature for isothermic measurements, and it is possible to change the temperature of the channel 14 and measurement chamber 12 over a chosen temperature range for scanning measurements.

FIG. 4 illustrates that in order to provide reference temperatures for the measurements it is proposed that at least one of the vessels 21r is used as a reference vessel, and that any reference vessel 21r is charged with inert material. In FIGS. 4a, 4b and 4c the opening of the device is in the lower part of the figure, so any temperature gradient "G" in the measurement chamber is likely to be according to the arrow "G" in the figures.

FIG. 4a illustrates an embodiment where two reference vessels 21r, 22r are used. The different vessels with samples are divided into groups according to the dotted line and the measurement results from each group are adjusted according to the measurements from the reference vessels.

FIG. 4b illustrates that reference vessels are positioned at the outer columns of vessels. In this embodiment the vessels can be divided into lines, where each reference vessel is used as reference to the vessels in its own line and on its own side of the dotted line in the figure.

FIG. 4c illustrates that half of the vessels 21r. 22r, . . . , 2mr are used as reference vessels and half of the vessels for samples. In this embodiment every vessel with samples can use adjacent reference vessels for measurement adjustments.

The inventive method proposes that the temperature within an outer chamber 6, schematically illustrated in FIG. 3, is kept at a lower temperature than that of the measurement chamber 12, where an outer container 5 which encloses, and is thermally isolated from, the first and second metal bodies 16, 17, is positioned within the outer chamber. It is proposed that the temperature difference between the outer chamber 6 and the measurement chamber 12 might be in the order of 5° C. or more.

With a multi-channel calorimetric system according to the inventive device and vessel assembly, using vessel plates of microtiter format, it is possible to perform parallel experiments and tests of cultivated cells. This ability enables performance of new types of calorimetric experiments as exemplified below:

a) Simultaneous measurements of thermal output from cultivated cells, rather than individual experiments, enables rational experimental design, for example performing dose-response curves.
b) Simultaneous measurements of thermal output from cultivated cells, rather than individual experiments, enables normalization of analysed values, a prerequisite for cell biological measurements.
c) The format enables measurements of thermal output from adherent cells, i.e. cells growing adherent to a surface. Previous calorimetric experiments on cultivated cells were restricted to cells growing in suspension or, cells adhering to micro-carriers, in which case normalization was almost impossible to achieve. Using the inventive device and method, both control of cell numbers and morphological state can be achieved, as well as normalization for each well individually.
d) The format enables usage of robotics when performing experiments.

A specific example of the use of the present invention is the following description if a dose-response experiment performed in an inventive device.

Cultivated 3T3-L1 cells were differentiated to white adipocytes and treated with insulin at five triplet concentrations. The experiment was divided in two parts, recording of the thermal power output of each well vessel before addition of insulin, basal metabolic rate, and after addition of insulin, induced metabolic increased activity.

The basal metabolic rates were recorded for 30 minutes. The microtiter plate was taken out from the instrument and insulin was added to the well vessels, triplets of five concentrations, randomly distributed among the used well vessels. After 30 min equilibration time the thermal power were recorded during 30 minutes.

The results from the two consecutive thermal power measurements were treated as s ratios between insulin induced metabolic activity and basal metabolic rate. In this way there is no need for counting the number of cells or perform any other normalisation procedure. The results are shown in FIG. 5.

It will be understood that the invention is not restricted to the aforedescribed and illustrated exemplifying embodiments thereof and that modifications can be made within the scope of the inventive concept as illustrated in the accompanying Claims.

The invention claimed is:

1. A device for the measurement of heat flow from at least one sample, said device being adapted to receive a multi well vessel assembly with samples in one or several vessels, said device comprising an opening for insertion of said vessel assembly into said device, a measurement chamber with a heat sink, a channel extending from said opening to said measurement chamber and a lid with a closing member for closing said opening during measurements, characterised in, that said opening and channel leads horizontally into said device, and that the height of said opening, channel and measurement chamber is only high enough to receive said vessel assembly.

2. A device according to claim 1, characterised in, that the height of said channel and measurement chamber is adaptable to the height of different vessel assemblies.

3. A device according to claim 1, characterised in, that the height of said opening, channel and measurement chamber exceeds the height of said vessel assembly by 5 mm or less.

4. A device according to claim 3, characterised in, that said first and second metal body and said lid are thermostated at the same temperature.

5. A device according to claim 4, characterised in, that said metal bodies are kept at constant temperature at a chosen experimental temperature for isothermic measurements.

6. A device according to claim 4, characterised in, that the temperature of said metal bodies is changed over a chosen temperature range for scanning measurements.

7. A device according to claim 1, characterised in, that said measurement chamber is made out of a cavity within a first metal body, that said channel is made out of a hole through a second metal body, and that said first and second metal bodies are thermally isolated from each other.

8. A device according to claim 7, characterised in, that an outer container encloses said first and second metal bodies, and that said container is thermally isolated from said first and second metal bodies.

9. A device according to claim 8, characterised in, that said container is a Dewar container.

10. A device according to claim 8, characterised in, that said outer container, with its first and second metal bodies, is positioned within an outer chamber, and that the temperature within said outer chamber is kept at a lower temperature than that of said measurement chamber.

11. A device according to claim 10, characterised in, that the temperature in said outer chamber is in the order of 5° C. or more below the temperature in said measurement chamber.

12. A device according to claim 7, characterised in, that said heat sink is made out of a third metal body positioned within said cavity, and that said third metal body is thermally isolated from said first metal body.

13. A device according to claim 12, characterised in, that said measurement chamber is divided into a first area, adapted for equilibration of a vessel assembly, and a second area, containing said heat sink and adapted to receive a vessel assembly during said measurement.

14. A device according to claim 13, characterised in, that thermal sensors are positioned on said heat sink so that every individual vessel within a vessel assembly is positioned on a thermal sensor as a vessel assembly is placed in said second area.

15. A device according to claim 14, characterised in, that the top surface of said third metal body is divided into pillars, and that one of said thermal sensors is positioned on top of each pillar.

16. A device according to claim 14, characterised in, that said thermal sensors are spring loaded on top of said heat sink.

17. A multi well vessel assembly with several vessels for the containing of samples, characterised in, that an outer bottom surface of each vessel is formed to provide a good thermal contact with a thermal sensor when put into a device according to claim 1.

18. A vessel assembly according to claim 17, characterised in, that each vessel within said vessel assembly is positioned so that they will be positioned on a thermal sensor.

19. A vessel assembly according to claim 17, characterised in, that each vessel is loosely fit into said vessel assembly.

20. A vessel assembly according to claim 17, characterised in, that said vessels are made out of glass.

21. A vessel assembly according to claim 17, characterised in, that said vessels are made out of stainless steel.

22. A vessel assembly according to claim 17, characterised in, that said vessels are made out of plastic.

23. A vessel assembly according to claim 17, characterised in, that said vessel assembly is disposable.

24. A vessel assembly according to claim 17, characterised in, that the vessel of said vessel assembly are disposable.

25. A method to measure the heat flow from at least one sample in a multi well vessel assembly, by means of a device comprising an opening for inserting said vessel assembly into said device, a measurement chamber with a heat sink, a channel extending from said opening to said measurement chamber and a lid with a closing member for closing said opening during measurements, characterised in, transporting said vessel assembly in a horizontal direction through said opening and channel, and into said measurement chamber to measure the heat flow.

26. A method according to claim 25, characterised in, that said channel and measurement chamber are kept constant at a chosen experimental temperature for isothermic measurements.

27. A method according to claim 25, characterised in, that the temperature of said channel and measurement chamber is changed over a chosen temperature range for scanning measurements.

28. A method according to claim 25, characterised in, that said vessel assembly is allowed to equilibrate in said channel before being transported into said measurement chamber, that said vessel assembly is allowed to equilibrate in a first area within said measurement chamber before being transported into a second area, containing said heat sink and adapted to receive a vessel assembly for measurements, and that said vessel assembly is allowed to equilibrate in said second area before the start of said measurement.

29. Method according to claim 28, characterised in, that said vessel assembly is allowed to equilibrate for a time period in the order of 10 minutes in said channel and said first area, and for a time period in the order of 30 minutes in said second area.

30. A method according to claim 25, characterised in, that at least one of said vessels is used as a reference vessel, and that said reference vessel is charged with inert material.

31. A method according to claim 30, characterised in, that half of said vessels are used as reference vessels and half of said vessels are used for samples.

32. A method according to claim 25, characterised in, that the temperature within an outer chamber is kept at a lower temperature than that of said measurement chamber, where an outer container which encloses, and is thermally isolated from, said measurement chamber and channel, is positioned within said outer chamber.

33. A method according to claim 32 characterised in, that the temperature difference between said outer chamber and said measurement chamber is in the of 5° C. or more.

* * * * *